United States Patent [19]
Millett et al.

[11] Patent Number: 5,724,254
[45] Date of Patent: Mar. 3, 1998

[54] APPARATUS AND METHOD FOR ANALYZING POWER PLANT WATER CHEMISTRY

[75] Inventors: Peter J. Millett, Half Moon Bay, Calif.; Gary D. Burns, Corapolis, Pa.; Gary E. Brobst, Sebastopol, Calif.

[73] Assignee: Electric Power Research Institute, Palo Alto, Calif.

[21] Appl. No.: 588,194

[22] Filed: Jan. 18, 1996

[51] Int. Cl.$^6$ .................................................. G01N 33/18
[52] U.S. Cl. ........................... 364/497; 395/914; 395/915
[58] Field of Search ..................... 364/496, 497, 364/500, 578; 395/911, 915, 914, 902, 50, 1, 11, 22

[56] References Cited

U.S. PATENT DOCUMENTS

| | | |
|---|---|---|
| 4,886,590 | 12/1989 | Tittle . |
| 4,943,161 | 7/1990 | Michaelis et al. . |
| 4,943,929 | 7/1990 | Simonoff . |
| 5,203,984 | 4/1993 | Sakai et al. . |
| 5,239,483 | 8/1993 | Weir . |

OTHER PUBLICATIONS

Suganuma et al., "Development of a Diagnostic Expert System for Secondary Water Chemistry" Artificial Intelligence in Nuclear Power Plants, pp. 299–310, 1990.

Kneile, "Wring More Information Out of Plant Data," Chemical Engineering, Mar. 1995, pp. 110–116.

EPRI chem Works™ Users Manual Vols. 1 & 2 (1995).

*Primary Examiner*—Ellis B. Ramirez
*Assistant Examiner*—M. Kemper
*Attorney, Agent, or Firm*—William S. Galliani; Flehr Hohbach Test Albritton & Herbert LLP

[57] ABSTRACT

A power plant water chemistry analysis apparatus and method relies upon water chemistry sensors to obtain power plant water chemistry data characterizing the chemical activity of a power plant water system. An analytical model processor is used to generate model predictions for the power plant water system. A statistical data fitting processor selects screened data from the power plant water chemistry data that corresponds to the model predictions. The screened data is processed by an artificial intelligence processor to derive power plant water chemistry diagnostic information. The artificial intelligence processor includes an expert system, rule base, plant water chemistry system simulator, and pattern recognition module.

16 Claims, 16 Drawing Sheets

EPRI chemWORKS – PWRSCS

File  Edit  Output  View  Window

Hideout Decomposition rsg.usr | sample.dep | rsg634.pwr | fig2.dta | 1e3

Grid

|         | Drain Tank No. 1 | Heater Outlet No. 1 | Condenser Liquid | Hotwell(CPD) | Air Eject Drain |
|---------|------------------|---------------------|------------------|--------------|-----------------|
| pH(t)   | 6.60 | 6.34 | 8.79 | 8.79 | 8.59 |
| pH(n)   | 5.65 | 5.60 | 6.64 | 6.64 | 6.39 |
| pH(25°C) | 9.57 | 9.51 | 9.48 | 9.48 | 9.79 |
| pH(25°C)w/o cat. | 5.65 | 6.14 | 6.61 | 6.61 | 6.50 |
| Sp. Cond. | 9.00 | 7.99 | 7.44 | 7.41 | 17.0 |
| Cat. Cond. | 0.88 | 0.29 | 0.10 | 0.10 | 0.13 |
| Na | 1.74e-2ppb | 1.34e-2ppb | 1.27e-4ppb | 1.26e-4ppb | 1.73e-3ppb |
| Cl | 3.48e-2ppb | 2.35e-2ppb | 2.54e-4ppb | 2.52e-4ppb | 3.46e-3ppb |
| OAc | 150 ppb | 43.9 ppb | 12.3 ppb | 12.2 ppb | 17.1 ppb |
| NH3 | 0.39 ppm | 0.50 ppm | 0.54 ppm | 0.54 ppm | 4.49 ppm |
| N2H4 | 93.1 ppb | 100 ppb | 21.8 ppb | 21.7 ppb | 17.6 ppm |
| Mpa | 0.93 ppm | 1.00 ppm | 1.01 ppm | 1.00 ppm | 0.47 ppm |
| Eta | 3.49 ppm | 2.00 ppm | 1.34 ppm | 1.33 ppm | 0.70 ppm |

FIG. 6

EPRI chemWORKS - PWRSCS

File  Edit  Output  View  Window

☒ Hideout
☒ Decomposition

[rsg.usr] [sample.dep] [rsg634.pwr] [fig2.dta]  1e3

Grid

|  | SG Blowdown | Main Steam | MSR Inlet LP | Turbine Inlet | Moisture Separator |
|---|---|---|---|---|---|
| pH(t) | 6.20 | 6.22 | 6.64 | N/A | 6.69 |
| pH(n) | 5.61 | 5.61 | 5.65 | N/A | 5.65 |
| pH(25°C) | 9.58 | 9.51 | 9.51 | 9.48 | 9.68 |
| pH(25°C)w/o cat. | 5.65 | 6.10 | 6.08 | 6.61 | 5.27 |
| Sp. Cond. | 9.07 | 7.92 | 7.89 | 7.44 | 11.5 |
| Cat. Cond. | 0.87 | 0.31 | 0.33 | 0.10 | 2.10 |
| Na | 1.00 ppb | 4.89e-3ppb | 4.89e-3ppb | 1.27e-4ppb | 5.06e-2ppb |
| Cl | 2.00 ppb | 9.80e-3ppb | 9.80e-3ppb | 2.54e-4ppb | 0.10 ppb |
| OAc | 145 ppb | 48.4 ppb | 50.9 ppb | 12.3 ppb | 421 ppb |
| NH3 | 0.23 ppm | 0.50 ppm | 0.50 ppm | 0.54 ppm | 8.64e-2ppm |
| N2H4 | 186 ppb | 49.4 ppb | 39.5 ppb | 21.8 ppb | 209 ppb |
| Mpa | 0.71 ppm | 0.99 ppm | 0.99 ppm | 1.01 ppm | 0.77 ppm |
| Eta | 4.28 ppm | 1.95 ppm | 1.93 ppm | 1.34 ppm | 7.60 ppm |

FIG. 7

EPRI chemWORKS – PWRSCS

File  Edit  Links  Species  Window

Hideout Decomposition  rsg.usr  sample.dep  rsg634.pwr  fig2.dta  1e3

Input

| Species | Units | | Sample | | CPD | BDE | CPE | Hideout |
|---|---|---|---|---|---|---|---|---|
| | In | Out | Loc | Conc. | Conc. | Conc. | Conc. | WH(lb/h) |
| Na | ppb | ppb | B | 2.0 | | 0 | 0 | 50000 |
| Cl | ppb | ppb | B | 3.1 | | 0 | 0 | 25000 |
| OAc | ppb | ppb | | | | | | |
| NH3 | ppm | ppm | F | 0.5 | | 0 | 0 | |
| N2H4 | ppb | ppb | F | 100 | | 0 | 0 | |
| Mpa | ppm | ppm | F | 1 | | 0 | 0 | |
| Eta | ppm | ppm | F | 2 | | 0 | 0 | |

FIG. 9

| EPRI chemWORKS - PWRSCS | | | |
|---|---|---|---|
| File Edit Output View Window | | | |
| ☒ Hideout | rsg.usr | sample.dep | rsg634.pwr | fig2.dta | 1e3 | | | |
| ☒ Decomposition | | | |

| Grid | | | |
|---|---|---|---|
| | Sources/Sinks(lb/h) | Hideout(lb/h) | SG Blowdown |
| pH(t) | | | 6.20 |
| pH(n) | | | 5.61 |
| pH(25°C) | | | 9.58 |
| pH(25°C)w/o cat. | | | 5.65 |
| Sp. Cond. | | | 9.07 |
| Cat. Cond. | | | 0.88 |
| Na | 1.01e-4 lb/h | 0.00e0 lb/h | 1.98 ppb |
| Cl | 1.62e-4 lb/h | 0.00e0 lb/h | 3.17 ppb |
| OAc | 6.38e-5 lb/h | 0.00e0 lb/h | 145 ppb |
| NH3 | 4.59 lb/h | 0.00e0 lb/h | 0.23 ppm |
| N2H4 | 1.16 lb/h | 0.00e0 lb/h | 186 ppb |
| Mpa | 8.73 lb/h | 0.00e0 lb/h | 0.71 ppm |
| Eta | 12.3 lb/h | 0.00e0 lb/h | 4.28 ppm |

FIG. 11

Grid

| | SG Blowdown | Moisture Separator | Heater Outlet No. 1 | Hotwell (CPD) |
|---|---|---|---|---|
| pH(t) | 6.30 | 6.80 | 6.43 | 8.88 |
| pH(n) | 5.61 | 5.65 | 5.60 | 6.64 |
| pH(25°C) | 9.72 | 9.82 | 9.62 | 9.57 |
| pH(25°C)w/o cat. | 5.34 | 5.01 | 5.83 | 6.42 |
| Sp. Cond. | 12.6 | 16.2 | 10.0 | 8.94 |
| Cat. Cond. | 1.80 | 3.83 | 0.58 | 0.15 |
| Na | 1.00 ppb | 5.06e-2ppb | 1.34e-2ppb | 1.26e-4ppb |
| Cl | 2.00 ppb | 0.10 ppb | 2.35e-2ppb | 2.52e-4ppb |
| OAc | 343 ppb | 922 ppb | 94.3ppb | 21.4 ppb |
| NH3 | 0.23 ppm | 8.41e-2ppm | 0.50 ppm | 0.54 ppb |
| N2H4 | 184 ppb | 208 ppb | 100 ppb | 21.8 ppb |
| Mpa | 0.70 ppm | 0.73 ppm | 1.00 ppm | 1.01 ppm |
| Eta | 8.39 ppm | 14.7 ppm | 4.00 ppm | 2.71 ppm |

FIG. 12

EPRI chemWORKS – PWRSCS

File  Edit  Output  View  Window

☒ Hideout  ☒ Decomposition rsg.usr | sample.dep | rsg634.pwr | fig2.dta | 1e3

Grid

|  | Cond. Inleak (lb/h) | SG Blowdown | Heater Outlet No. 1 | Hotwell (CPD) |
|---|---|---|---|---|
| pH(t) |  | 6.30 | 6.42 | 8.88 |
| pH(n) |  | 5.61 | 5.60 | 6.64 |
| pH(25°C) |  | 9.72 | 9.62 | 9.57 |
| pH(25°C)w/e cat. |  | 5.30 | 5.83 | 6.41 |
| Sp. Cond. |  | 12.6 | 10.0 | 8.94 |
| Cat. Cond. |  | 2.00 | 0.58 | 0.16 |
| Na | 8.69e-4 lb/h | 9.70 ppb | 0.13 ppb | 0.10 ppb |
| Cl | 1.57e-3 lb/h | 21.6 ppb | 0.25 ppb | 0.19 ppb |
| OAc | 0.00e0 lb/h | 343 ppb | 94.4 ppb | 21.5 ppb |
| NH3 | 0.00e0 lb/h | 0.23 ppm | 0.50 ppm | 0.54 ppm |
| N2H4 | 0.00e0 lb/h | 184 ppb | 100 ppb | 21.8 ppb |
| Mpa | 0.00e0 lb/h | 0.70 ppm | 1.00 ppm | 1.01 ppm |
| Eta | 0.00e0 lb/h | 8.40 ppm | 4.00 ppm | 2.71 ppm |

FIG. 14

EPRI chemWORKS – PWRSCS

File Edit Output View Window
Hideout Decomposition [rsg.usr] [sample.dep] [rsg634.pwr] [fig2.dta] 1e3

Grid

| Sources/Sinks(lb/h) | SG Blowdown | Heater Outlet No. 1 | Hotwell (CPD) |
|---|---|---|---|
| pH(t) | 6.35 | 6.49 | 8.95 |
| pH(n) | 5.60 | 5.60 | 6.64 |
| pH(25°C) | 9.81 | 9.69 | 9.64 |
| pH(25°C)w/o cat. | 5.15 | 5.64 | 6.27 |
| Sp. Cond. | 15.5 | 11.9 | 10.4 |
| Cat. Cond. | 2.78 | 0.90 | 0.21 |
| Na | 1.01e-4 lb/h | 1.00 ppb | 1.34e-2 ppb | 1.26e-4 ppb |
| Cl | 1.62e4 lb/h | 2.00 ppb | 2.35e-2 ppb | 2.52e-4 ppb |
| OAc | 2.49e4 lb/h | 595 ppb | 154 ppb | 31.2 ppb |
| NH3 | 4.59 lb/h | 0.23 ppm | 0.50 ppm | 0.54 ppm |
| N2H4 | 1.16 lb/h | 183 ppb | 100 ppb | 21.9 ppb |
| Mpa | 8.79 lb/h | 0.70 ppm | 1.00 ppm | 1.01 ppm |
| Eta | 38.8 lb/h | 12.8 ppm | 6.14 ppm | 4.20 ppm |

FIG. 15

| | Sources/Sinks(lb/h) | SG Blowdown | Heater Outlet No. 1 | Heater Outlet No. 6 | Hotwell(CPD) |
|---|---|---|---|---|---|
| pH(t) | | 6.13 | 6.30 | 8.08 | 8.77 |
| pH(n) | | 5.61 | 5.60 | 6.30 | 6.64 |
| pH(25°C) | | 9.53 | 9.49 | 9.48 | 9.46 |
| pH(25°C)w/o cat. | | 5.15 | 5.51 | 6.03 | 5.97 |
| Sp. Cond. | | 8.65 | 7.78 | 7.50 | 7.27 |
| Cat. Cond. | | 2.78 | 1.20 | 0.37 | 0.42 |
| Na | 1.01e-4 lb/h | 1.00 ppb | 1.34e-2ppb | 1.20e-2ppb | 1.26e-4ppb |
| Cl | 1.62e-4 lb/h | 2.00 ppb | 2.35e-2ppb | 1.92e-2ppb | 2.52e-4ppb |
| OAc | 9.83e-5lb/h | 595 ppb | 216 ppb | 57.6 ppb | 67.1 ppb |
| NH3 | 4.58 lb/h | 0.23 ppm | 0.50 ppm | 0.54 ppm | 0.54 ppm |
| N2H4 | 1.16 lb/h | 188 ppb | 100 ppb | 137 ppb | 21.4 ppb |
| Mpa | 8.65 lb/h | 0.72 ppm | 1.00 ppm | 1.02 ppm | 0.99 ppm |
| Eta | 12.0 lb/h | 4.38 ppm | 2.00 ppm | 1.42 ppm | 1.28 ppm |

FIG. 16

APPARATUS AND METHOD FOR ANALYZING POWER PLANT WATER CHEMISTRY

BRIEF DESCRIPTION OF THE INVENTION

This invention relates generally to power plant water systems. More particularly, this invention relates to an automated system for screening and analyzing power plant water chemistry data to diagnose power plant water chemistry problems.

BACKGROUND OF THE INVENTION

Many power plants operate by heating water to produce steam. The steam is then used to drive a turbine. The turbine rotates a generator that is used to produce electricity.

The water chemistry in power plants of this type is typically monitored at several locations within the system. Trend graphs are then constructed using the collected chemistry data. Trained chemistry personnel review the data to insure that the impurity and additive levels are within prescriptive specifications and to identify underlying trends in the data which may indicate abnormal operation of the system.

Data acquisition systems have been developed for collecting and displaying power plant water chemistry data. Rule based expert systems have also been developed to identify inconsistencies in the data and warn of possible abnormal conditions. Existing expert systems are limited to rudimentary analyses of chemistry data.

It would be highly desirable to improve existing prior art techniques of analyzing power plant water chemistry. In particular, it would be highly desirable to provide an automated technique for improving the reliability of power plant water chemistry data. In addition, it would be highly desirable to provide an automated technique for assessing power plant water chemistry data to diagnose problems therein.

SUMMARY OF THE INVENTION

The invention is a power plant water chemistry analysis apparatus and method. The apparatus relies upon water chemistry sensors to obtain power plant water chemistry data characterizing the chemical activity of a power plant water system. An analytical model processor is used to generate model predictions for the power plant water system. A statistical data fitting processor selects screened data from the power plant water chemistry data that corresponds to the model predictions. The screened data is processed by an artificial intelligence processor to derive plant water chemistry diagnostic information. The artificial intelligence processor includes an expert system, rule base, plant water chemistry system simulator, and pattern recognition module.

The invention is used to diagnose normal and abnormal conditions in power plant water systems. Alone, or in conjunction with on-line data acquisition systems, the invention is used to minimize the amount of data which must be collected to properly account for the chemical state of the power plant water system. The invention greatly reduces costs associated with both instrumentation and the staffing required to maintain a water chemistry program. The system also provides information on the chemical state of the system in locations where measurements cannot be easily or economically made. This information is used in conjunction with knowledge of the degradation of system materials to minimize the impact of chemical action on power plant operation.

BRIEF DESCRIPTION OF THE DRAWINGS

For a better understanding of the nature and objects of the invention, reference should be made to the following detailed description taken in conjunction with the accompanying drawings, in which:

FIG. 6 illustrates a graphical user interface displaying chemical species distribution data corresponding to the data of FIG. 5.

FIG. 7 illustrates a graphical user interface displaying chemical species distribution data corresponding to the data of FIG. 5.

FIG. 9 illustrates a graphical user interface displaying sodium and chloride increase in accordance with Example 1 discussed below.

FIG. 11 illustrates a graphical user interface displaying hideout rates output information in accordance with Example 1 discussed below.

FIG. 12 illustrates a graphical user interface displaying data showing specific conductivity increases in accordance with Example 2 discussed below.

FIG. 14 illustrates a graphical user interface displaying condenser leak output information in accordance with Example 3 discussed below.

FIG. 15 illustrates a graphical user interface displaying the effect of changes in ETA concentration on acetate level as described in Example 4 discussed below.

FIG. 16 illustrates a graphical user interface displaying the effect of changing decomposition rate constants on acetate level as described in Example 4 discussed below.

Like reference numerals refer to corresponding parts throughout the several views of the drawings.

DETAILED DESCRIPTION OF THE INVENTION

Figure 1:
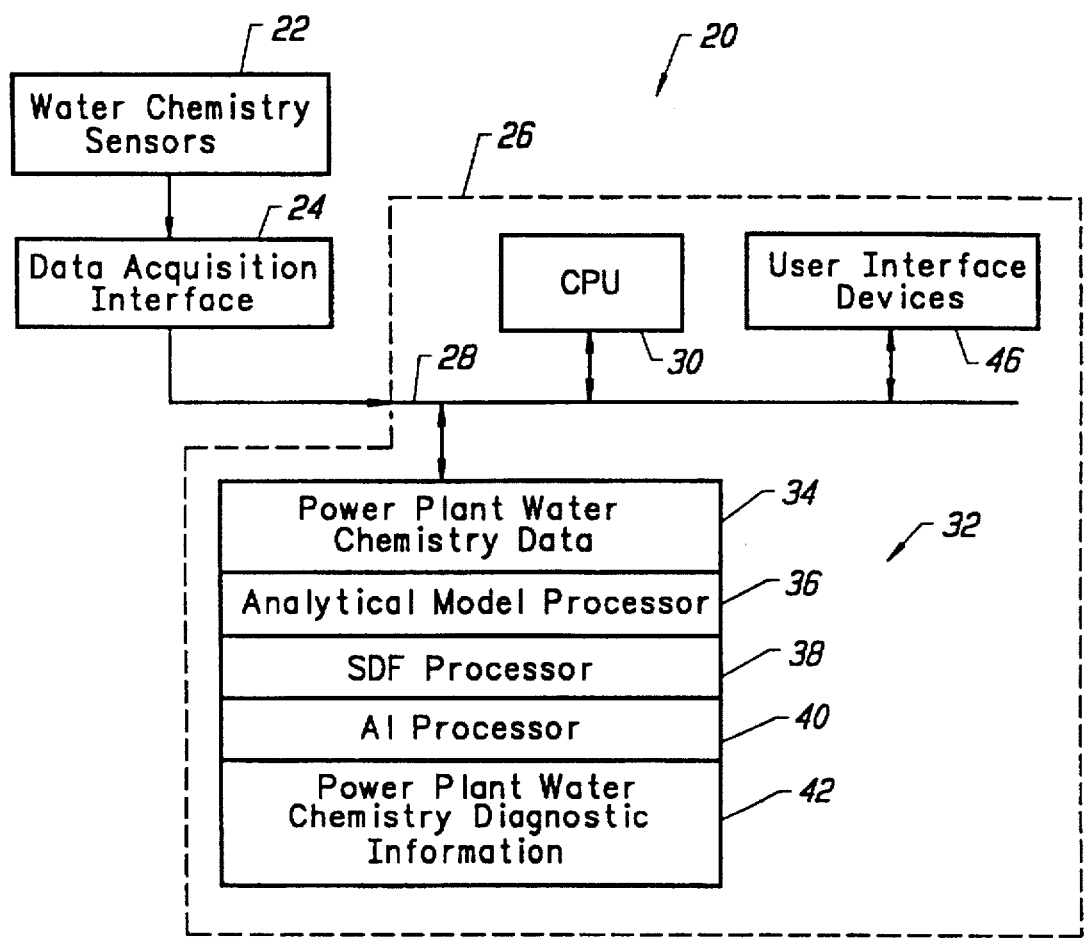
FIG. 1 illustrates a plant water chemistry analysis apparatus in accordance with the invention.

FIG. 1 illustrates a power plant water chemistry analysis apparatus 20 in accordance with the present invention. The apparatus 20 includes a set of water chemistry sensors 22 positioned in a power plant (not shown). The water chemistry sensor 22 are connected to a data acquisition interface 24 which digitizes the information and passes it to a computer 26 in the form of power plant water chemistry data.

The computer 26 includes a system bus 28 which receives the power plant water chemistry data. A central processing unit (CPU) 30 directs the power plant water chemistry data to a memory 32, where it is stored.

The CPU 30 executes a set of programs stored in the memory 32. The executable programs stored in the memory 32 include an analytical model processor 36, a statistical data fitting (SDF) processor 38, and an artificial intelligence processor 40. These programs operate in accordance with the CPU 30 to generate power plant water chemistry diagnostic information 42.

User interface devices 46 include standard input and output devices such as a keyboard, mouse, video monitor, printer, etc. The user interface devices 46 are used to modify and run the executable programs 36, 38, and 40; the user interface devices 46 also function to convey the power plant water chemistry diagnostic information 42.

The independent operation of water chemistry sensors 22, a data acquisition interface 24, and a computer 26 is known in the art. The present invention is directed toward the combination of these elements. More particularly, the invention is directed toward the operation of the water chemistry sensors 22 and the data acquisition interface 24 in connection with the executable programs of the computer 26.

Figure 2:
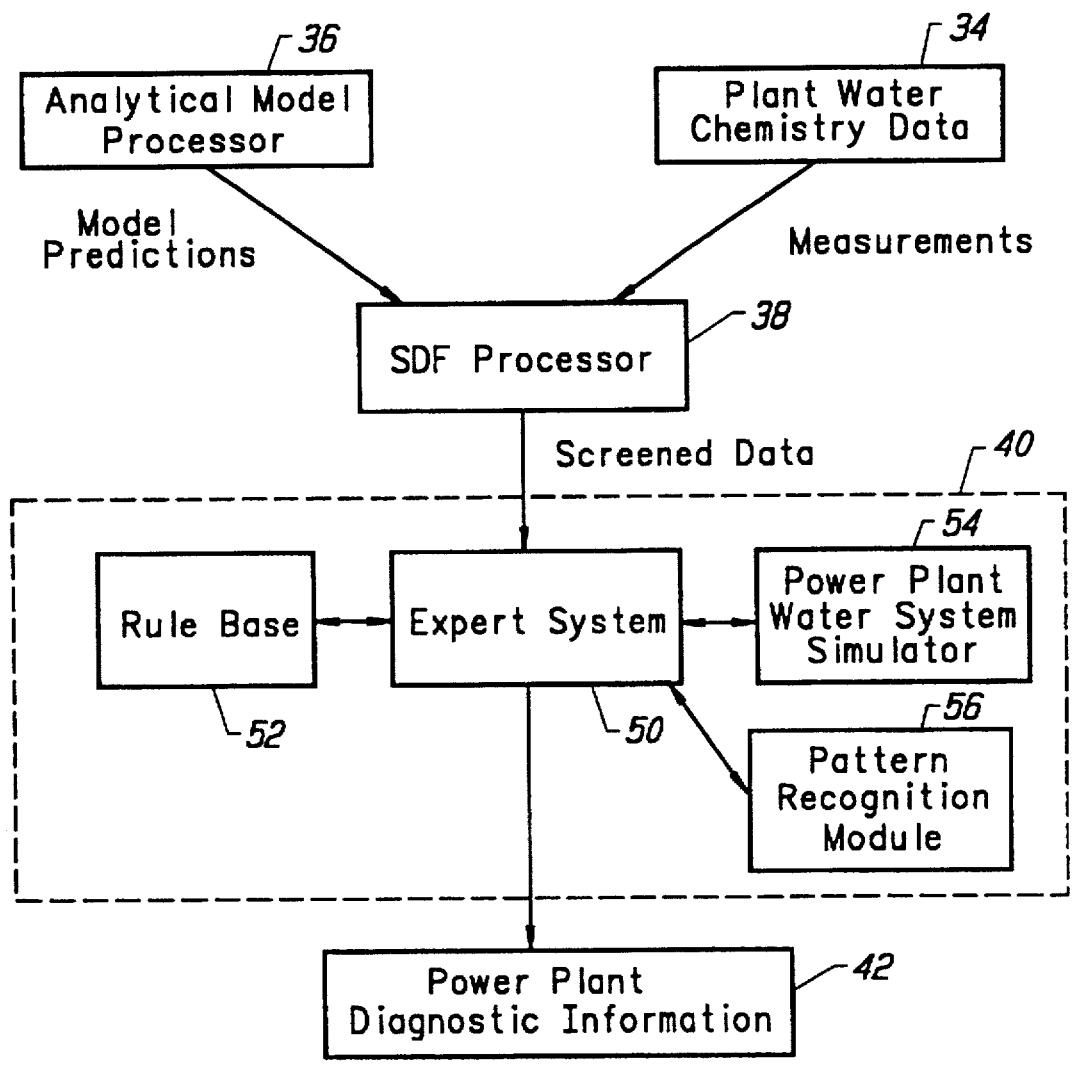
FIG. 2 illustrates the processing steps associated with the apparatus of FIG. 1.

FIG. 2 illustrates the processing associated with the present invention. In particular, FIG. 2 illustrates the processing associated with the different data and executable programs shown in FIG. 1. The analytical model processor 36 is a prior art device. For example, the EPRI chemWORKS™ software tools from the Electric Power Research Institute, Palo Alto, Calif., may be used as the analytical model processor 36. The EPRI chemWORKS™ software tools use plant specific specifications and sophisticated analytical models to describe the chemical state of a power plant water cycle. More particularly, the chemical state of the power plant water cycle is assessed with analytical models based on material balance constraints, multi-component equilibrium considerations and chemical kinetic information.

Figure 3:
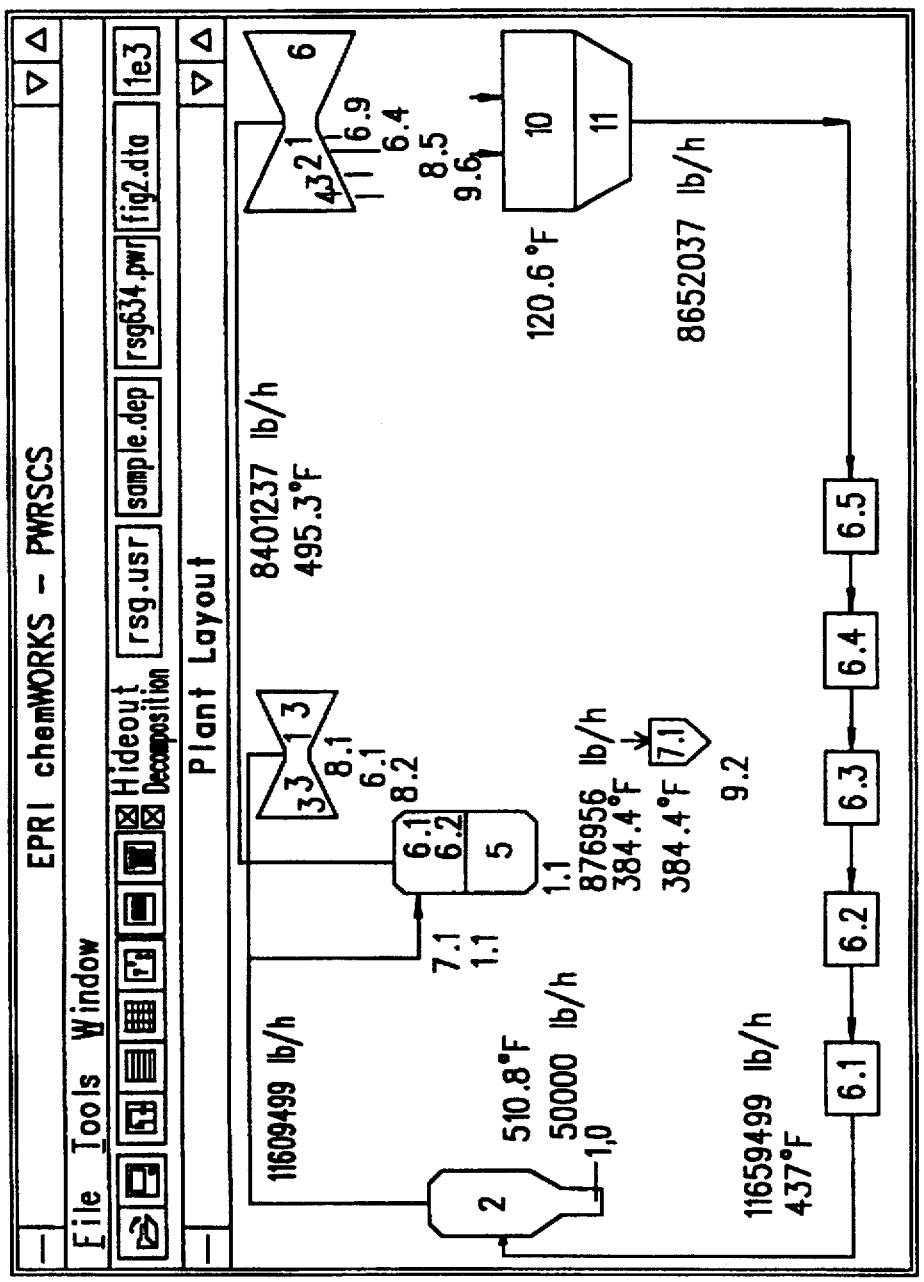
FIG. 3 illustrates an example graphical user interface which can be used with the invention to specify a plant layout and heat balance parameters.

FIG. 3 illustrates a user interface associated with the EPRI chemWORKS™ software tools. Conventional programming techniques are used to allow a user to specify a detailed description of the piping components of a power plant water system. Thus, fluid flow, thermal conditions, and all interconnections between piping systems are established through the graphical user interface. In particular, FIG. 3 shows a typical piping arrangement and the required heat balance information for the secondary system of a pressurized water reactor (PWR). The components shown in FIG. 3 include: a steam generator blowdown drain 1, a steam generator 2, a high pressure turbine 3, a low pressure turbine 4, a moisture separator 5, a reheater stage 6, a drain tank 7, a feedwater heater 8, a feedwater line 9, a condenser 10, and a hotwell 11. FIG. 3 and all subsequent figures are input or output screens associated with the graphical user interface of the EPRI chemWORKS™ software tools. Thus, as will be explained below, the EPRI chemWORKS™ software tools may be incorporated with the other elements of the invention.

Figure 4:
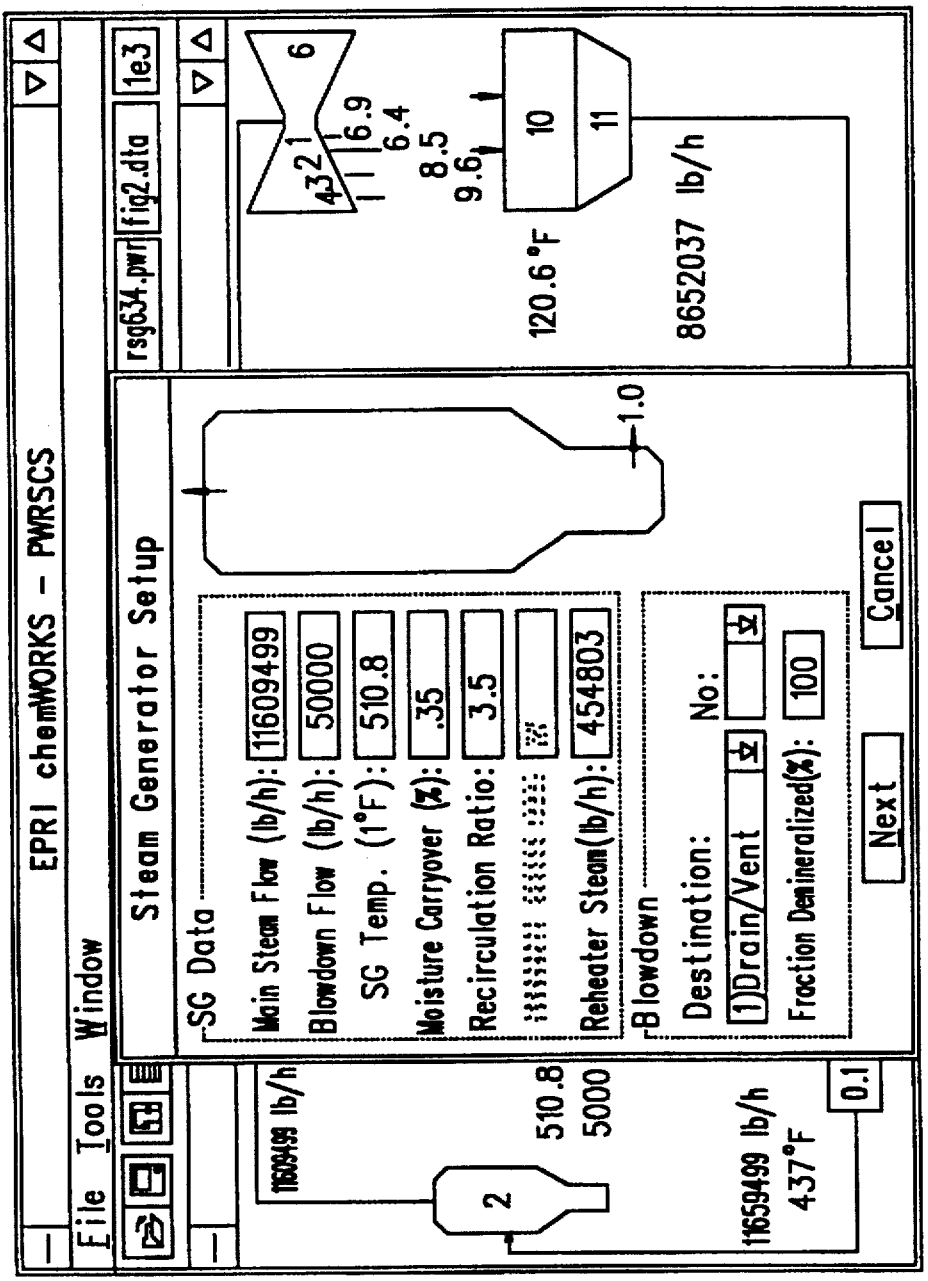
FIG. 4 illustrates an example graphical user interface for a steam generator specification screen corresponding to the system of FIG. 3.

FIG. 4 shows the input screen for the steam generator shown in FIG. 3. Similar screens exist for all of the components shown in FIG. 3.

Prior art analytical model processor 36, such as the EPRI chemWORKS™ software tools, have been used in a stand-alone fashion to determine the optimum water chemistry conditions for a system. The problem with this approach is that optimum water chemistry conditions can only be obtained when the user can specify some objective function. Thus, the analytical models cannot be used independently for diagnosing plant conditions.

The present invention extends the capabilities of existing analytical model processors, such as the EPRI chemWORKS™ software tools, by combining actual plant measurements with the analytical tools, selecting screened data from the plant measurements and model predictions of the analytical tools, and analyzing the screened data to yield power plant water chemistry diagnostic information. This processing is shown in FIG. 2.

FIG. 2 illustrates that the analytical model processor 36 generates model predictions. As indicated above, in the prior art, these model predictions stood alone. That is, the analytical model processor 36 was used solely for the purpose of generating the model predictions, which were then analyzed independently. As shown in FIG. 2, in accordance with the invention, the model predictions are combined with power plant water chemistry data 34 obtained from the water chemistry sensors 22. The model predictions and the power plant water chemistry data 34 are processed by a statistical data fitting (SDF) processor 38 to yield screened data.

There are a number of advantages associated with this approach. First, the limited role of the prior art analytical model processor 36 is extended. As will be discussed below, the analytical model processor 36 is no longer a standalone predictive device, instead its abilities are utilized in actually diagnosing plant water chemistry problems. Next, the validity of the plant water chemistry data 34 can be improved by relying upon the information available from the analytical model processor 36. That is, the combination of the model predictions and the plant measurements (plant water chemistry data) results in an over specified system, which can be used to obtain more accurate information.

The analytical model processor 36 provides system chemistry model predictions from a small number of unknowns and/or plant specific factors. The water chemistry sensors 22 are used to make numerous measurements in the process streams, such that the number of knowns (e.g. measurements) far exceeds the number of unknowns (in the model). Because the process measurements and some of the factors in the model are uncertain, the best or most certain model predictions are used to qualify the least certain measurements and vice-versa.

The SDF processor 38 permits interchangeability between the independent variables (e.g. plant measurements) and dependent variables (e.g. model predictions). Thus, the SDF processor 38 determines the statistical best fit of the plant measurements that satisfy the constraints given by the model predictions. A statistical data fitting technique that can be used in accordance with the invention is described in R. Kneile, "Wring More Information out of Plant Data", Chemical Engineering, March 1995, pp. 110–116.

Figure 5:
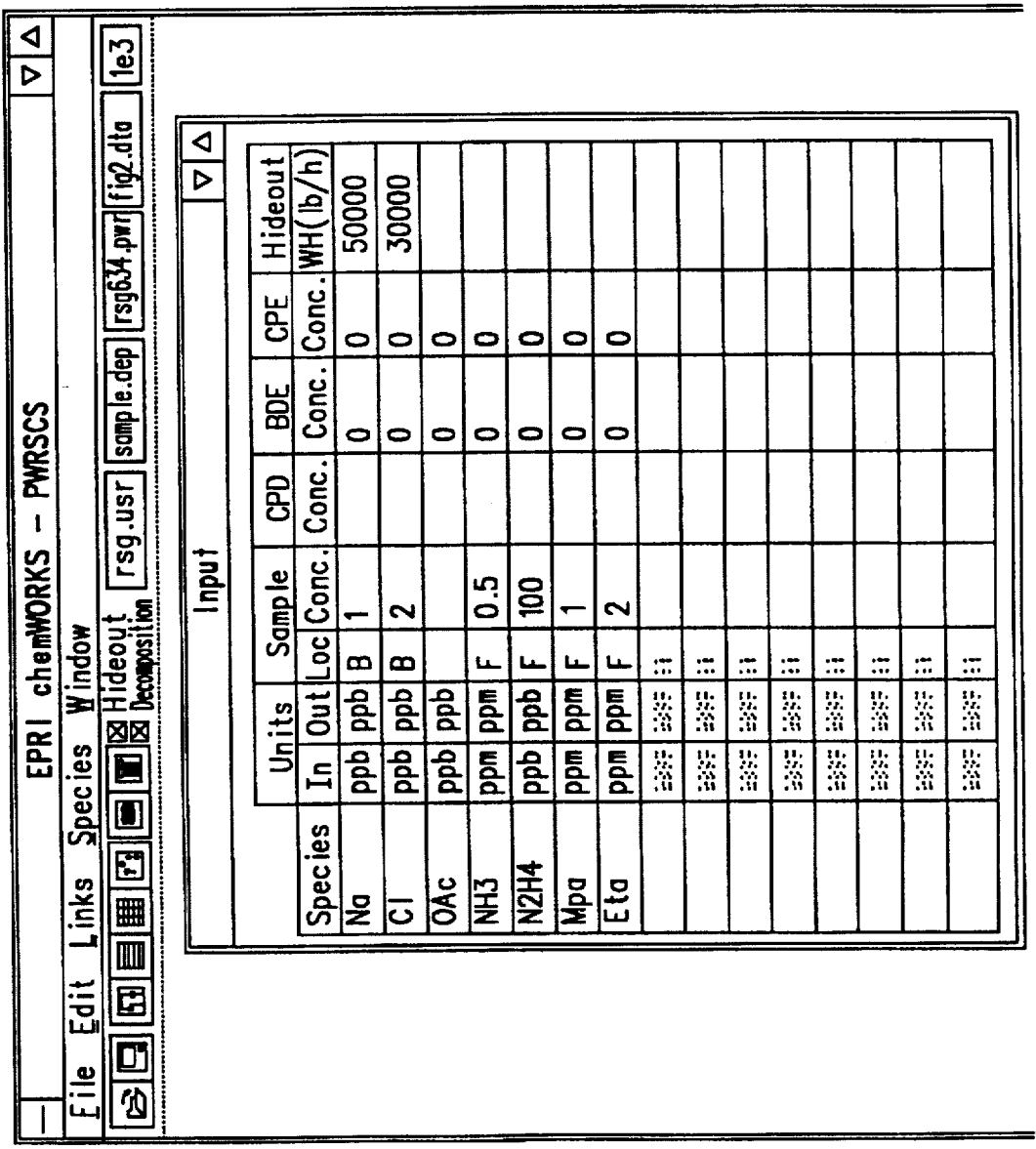
FIG. 5 illustrates a graphical user interface that may be used to display chemical species input information processed in accordance with the invention.

The screened data generated by the SDF processor 38 is applied to the artificial intelligence processor 40. FIG. 5 shows a sample input screen corresponding to the system of FIG. 3. The screen shows the known or measured concentrations in the plant water/steam cycle. (The measured species shown in FIG. 3 include Sodium (Na), chloride (Cl), ammonia (NH3), hydrazine (N2H4), methoxypropylamine (Mpa), and ethanolamine (Eta); "Sample Loc" indicates the location that the input is being defined, so that "B" indicates steam generator blowdown and "F" indicates feedwater; "Conc." represents the species concentration in input units; "CPD" is the condensate pump discharge concentration of a species; "BDE" is the blowdown demineralizer effluent concentration of a species; "CPE" is the condensate polisher effluent concentration of a species; and "Hideout" defines loss of species in a steam generator.)

These inputs are typically received from the SDF processor 38, but may also come from the water chemistry sensors. That is, the preferable embodiment of the invention uses screened data from the SDF processor 38. However, the invention is also operative with direct power plant water chemistry data obtained from the water chemistry sensors 22.

The artificial intelligence processor 40 performs a number of operations. First, it analyzes the screened data to identify any power plant problems. If a problem exists, it attempts to locate the problem. This is done by relying upon an expert system rule base 52. The operation of the rule base is sometimes supplemented by queries to the user of the system. The problem solving operation may also be supplemented with the use of a power plant water chemistry system simulator 54. The simulator 54 is used to test different proposed solutions derived by the expert system 50. The expert system also provides information on optimizing the data collection process. Finally, the artificial intelligence processor 40 includes a pattern recognition module 56. The pattern recognition module 56 is used to determine whether changes in chemistry parameters are consistent with past history or if instrumentation failure is likely. Preferably, the pattern recognition module 56 is implemented as a neural network.

The components and operation of the artificial intelligence processor 40 have now been described. Attention presently turns toward a more detailed discussion of the processor 40 components, which is followed by a set of examples to more fully demonstrate the operation of the invention.

The expert system 50 identifies chemical excursions and other abnormal activities. The expert system 50 attempts to attribute such a condition to a failure in the power plant water system. Preferably, the first step in this process is to determine which model predictions and which measurements are the most certain. This analysis is performed with the assistance of the rule base 52 and the results form the SDF processor 38. For example, the rule base may specify that instrumentation which has the longest operating period between calibrations is the least reliable. After the best data is selected with the assistance of the rule base 52, the rule base 52 is once again invoked to correlate the selected data with different plant conditions and permissible operations. For example, rules in the rule base 52 may provide thresholds that best fit plant measurements (screened data) should not exceed. When a threshold of this type is exceeded, the expert system 50 concludes that the corresponding instrument is not working properly.

The rule base 52 also includes information regarding actions to be taken in the presence of an identified anomalous condition. The suggested actions may be displayed on a video monitor of the user interface devices 46. Preferably, the suggested actions are initially tested with the use of the power plant water chemistry system simulator 54.

The simulator 54 solves mass balances and multicomponent equilibrium equations to determine the chemical speciation at points throughout the plant water system. The simulator 54 is invoked to evaluate the specific response throughout the plant to changes in additives or impurity concentrations.

Figure 8:
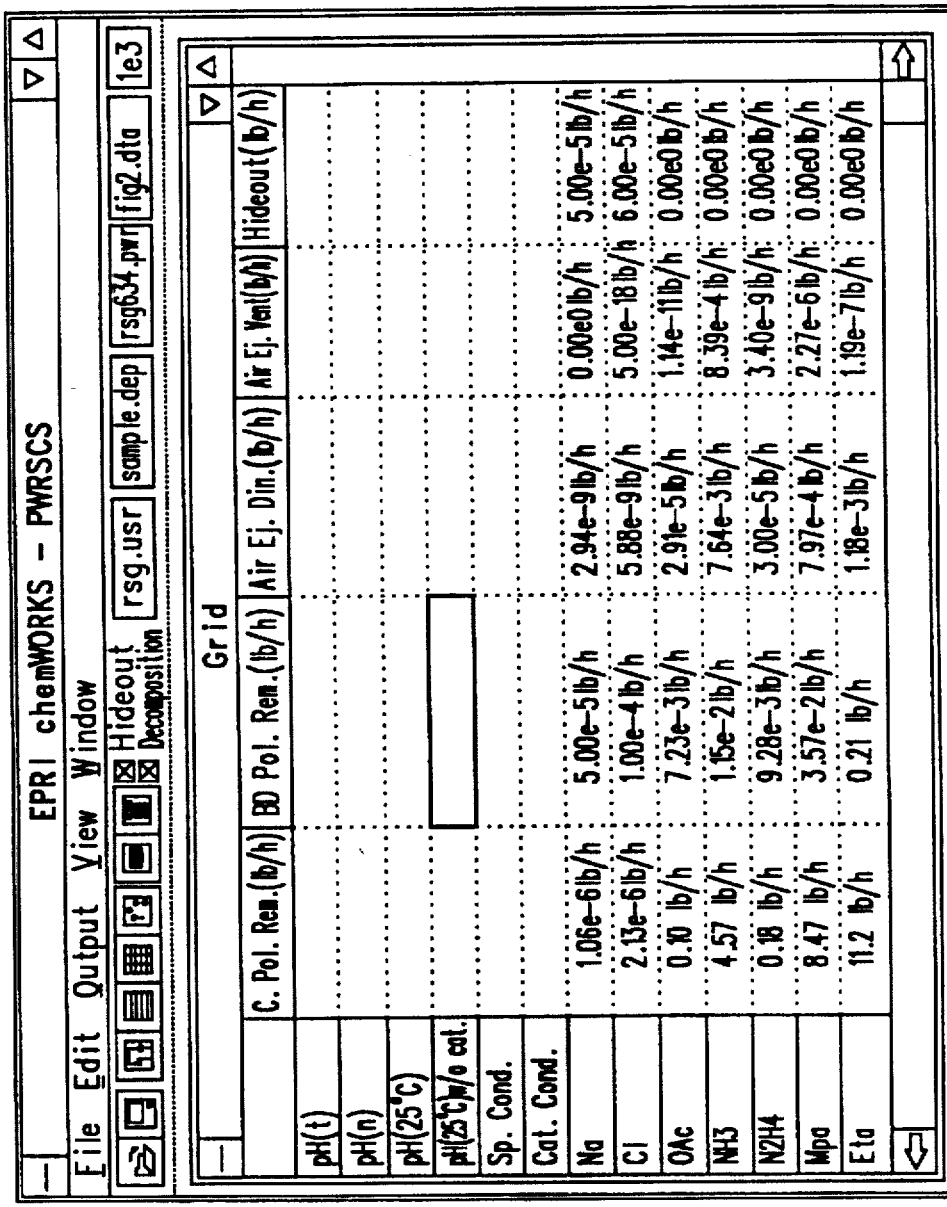
FIG. 8 illustrates a graphical user interface displaying system material balance data corresponding to the data of FIG. 5.

The foregoing descriptions are more fully appreciated with reference to the following examples. FIGS. 6 and 7 show the calculated distribution at selected locations of the species specified by the input conditions in FIGS. 3 and 4. FIG. 8 shows how the overall system material balances are met to achieve the steady state concentrations specified by FIG. 4. This information is referenced in the following examples.

EXAMPLE 1: ANALYSIS OF SODIUM AND CHLORIDE CONCENTRATION INCREASE IN BOILER WATER DUE TO CHANGES IN RATES OF HIDEOUT IN THE BOILER

A power plant normally operates with some steady-state level of impurities such as sodium and chloride in the water/steam cycle. Specifications for the maximum levels of impurities allowed are provided by the equipment supplier or in industry guidelines. There is generally no concern if the levels are below the specifications or if they are not trending upward. Often though, the levels increase for various reasons, such as condenser leakage or malfunctioning of condensate and/or makeup demineralizers. The behavior of impurities in the system can change due to fouling of heat transfer surfaces or due to other changes in plant operating conditions. This can result in an increase in the observed level of impurities in the system. It is imperative that plant operators be able to quickly assess the reasons for changes in impurity levels so that corrective actions can be taken and corrosion problems associated with the impurities can be avoided.

For example, assume that a plant is operating with the baseline chemistry shown in FIGS. 5–8. The expert system 50, rule base 52, and the simulator 54 are used to evaluate the most probable cause for an increase in sodium and/or chloride in the boiler water.

Preferably, the SDF processor 38 is used to establish the baseline chemistry data shown in FIG. 5. In this example, the source of a gradual measured increase in sodium in the blowdown from 1 to 2 ppb, and chloride from 2 to 3.2 ppb will be evaluated.

The input conditions for the model for this new chemistry are shown in FIG. 9. The first step is to verify that the measured increases for sodium and chloride are valid. The SDF processor 38 and the rule base 52 are used to verify the measurements. At a minimum, the rule base 52 consists of the following rules: 1) is the calibration of the sodium, (and chloride) instrument that is indicating an increase up to date?, 2) has the slope of the measured value of sodium (and chloride) been positive for a number of measurements?, 3) is the plant operating at steady-state?, and 4) does the screened data (from the SDF processor 38) confirm that the change in the measured sodium (and chloride) level is greater than the relative error in the measurements?

Using crisp or fuzzy logic techniques, the sodium (and chloride) concentrations are judged as being unchanged or as having increased, within some calculated uncertainty limits. A similar test is performed for other measured parameters such as sulfate and conductivity, since their values will not be constant, but may either fluctuate randomly or have increased at a different slope than sodium and/or chloride. The makeup of the impurity source is determined to be those species which have increased above the baseline.

Once the methodology described above has been employed to insure the measured increase is valid, an analysis of the cause of the increase is initiated. Specifically, the simulator 54 is run under several varied conditions to determine what parameters in the model (specified by the analytical model processor 36) would have to change from the baseline conditions specified in FIGS. 3–8 to give the new chemistry of FIG. 9.

Figure 10:
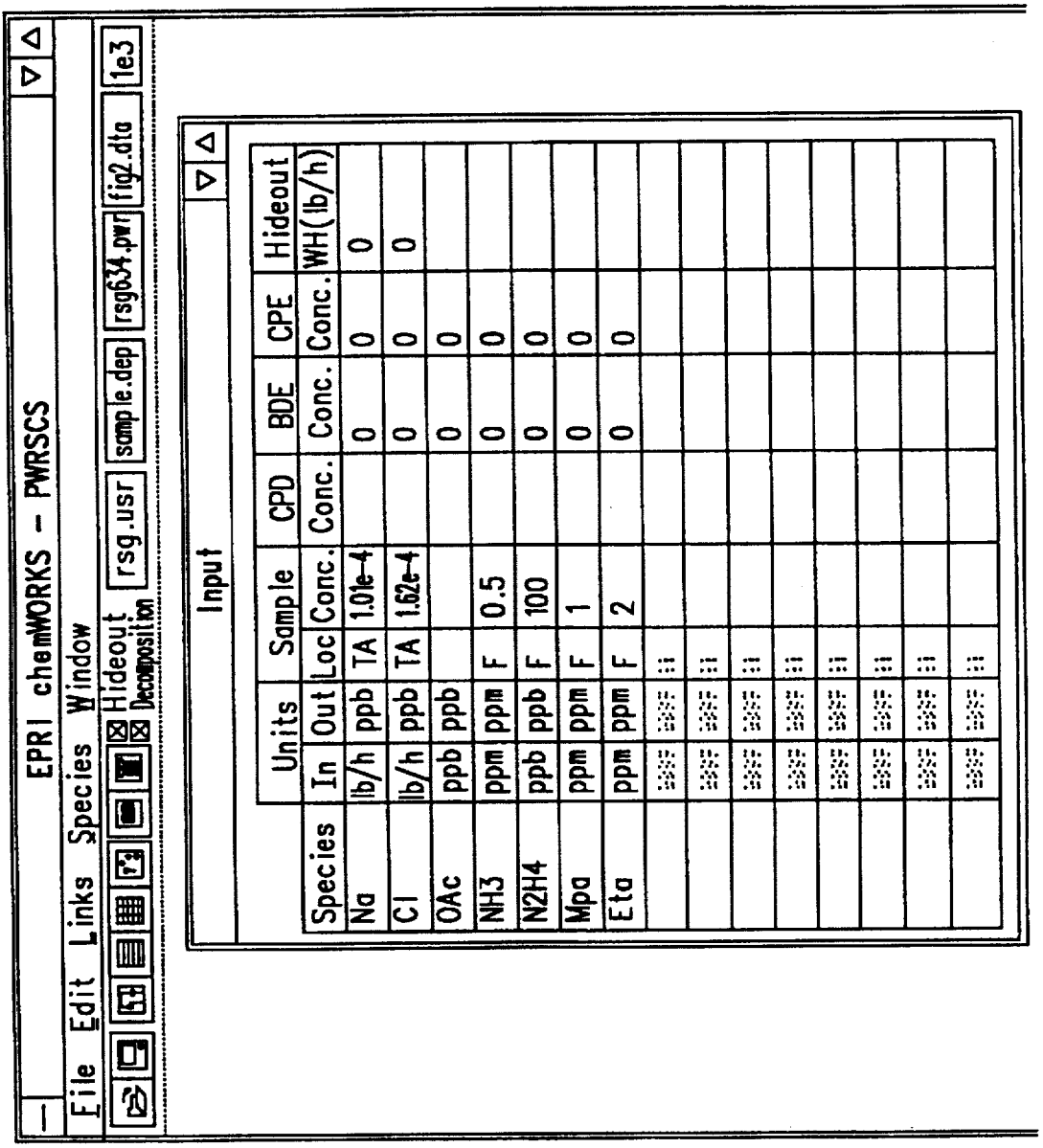
FIG. 10 illustrates a graphical user interface displaying sodium and chloride source information in accordance with Example 1 discussed below.

The first step is to determine if the change in measured values is due to ingress of impurities into the steam generator above the baseline condition or due to a change in the behavior of the impurities within the steam generator. In the latter case, the specified sodium and chloride source terms given by FIG. 8 are still valid (FIG. 8 shows output of species removed in lb/hr from the system via different removal locations). The input to the model under this scenario is shown in FIG. 10. Specifically, the source terms for sodium and chloride calculated for the baseline chemistry are specified as the input conditions to the model. Steam generator parameters such as the moisture carryover, hideout rates and blowdown rate can be varied using the input screen shown in FIG. 4 and the resulting steam generator sodium and chloride concentrations can be compared to the new measured steam generator values. If the predicted values are within a prescribed tolerance of the measured values, then a suitable rule is fired corresponding to the model parameter (e.g. moisture carryover, hideout rate or blowdown flow) which was changed.

For example, FIG. 11 shows the output for the steam generator blowdown when the hideout rates are decreased to zero. The predicted values of sodium and chloride are very close to the new measured values. However, the hideout rates are not expected to decrease with time, so the rule is fired with a low probability. Since the changes in moisture carryover or blowdown flow did not give the correct response, these parameters are not considered further, or the rules are fired with a low probability. The "probability factor" for each rule is dependent on how well the predicted values from the model matched the observed or measured values.

The next step is to check the value of the measured feedwater concentrations of sodium and chloride versus the predicted concentrations or the baseline case, as shown in FIG. 6. (In FIG. 6, "pH(t)" indicates pH at the temperature of the component; "pH(n)" is the neutral pH of water at the temperature of the component; "pH(25C)" is the pH at 25° C.; "pH(25C)w.o. cat" is the pH at 25° C. if cations are excluded from calculation; "Sp. Cond." is the specific conductivity of the solution; and "Cat. Cond." is the cation conductivity of the solution.)

In this case, although not shown here, the measured values confirm that the feedwater chemistry has not changed. This strengthens the probability that the increase in steam generator sodium and chloride is a result of a decrease in hideout rates. The expert system 50 then uses the interface devices 46 to prompt the user with a series of inquiries with appropriate weighting factors regarding ways in which the hideout factors could decrease (e.g. recent plant shutdowns, chemical cleaning of boilers, change in molar ratio, etc.). In this case, the expert system 50 might conclude that the hideout factors decreased after a plant trip.

EXAMPLE 2: DIAGNOSIS OF OVER FEED OF PH CONTROL AGENT IN THE FEEDWATER

Overfeeding the pH control agent in a power plant can result in several problems. Besides the obvious expense of the pH chemicals, elevated pHs can result in the early exhaustion of demineralizers and the accelerated corrosion of copper based piping systems.

In this example, the plant is operating under the baseline conditions of FIGS. 5–8. The specific conductivity measured in the feedwater and steam generator blowdown increases to the values shown in FIG. 12.

Preferably, the SDF processor 38 is used to insure that the measured changes in these parameters are consistent and exceed the errors established by the SDF algorithm. An increase in specific conductivity can result from a change in impurity or additive concentration in the system or due to a change in the decomposition of certain additives in the system (see example 4). In this case, the SDF algorithm executed by the SDF processor established that all measured species other than the specific conductivity have not changed (note: not all parameters shown in FIG. 12 are actually measured in the plant).

The expert system 50 concludes the source of the increased conductivity must be from a parameter which is not directly measured. Thus, the simulator 54 is run to evaluate the specific conductivity response throughout the plant to changes in additives in the feedwater whose concentrations are not directly measured. In this case, those additives are ethanolamine (ETA), methoxy propyl amine (MPA) and hydrazine. After the code executes several runs, the expert system 50 determines that the only change in additive concentration which could change the specific conductivity by the measured amount in the feedwater and steam generator blowdown is ETA. The expert system 50 concludes that good agreement can be achieved between the measured specific conductivity and the predicted specific conductivity by changing the feedwater concentration of ETA from 2 to 4 ppm (see FIG. 12). The expert system 50 then indicates to the operator (through the user interface devices 46) that it is likely that the ETA concentration has increased by a factor of 2. The operator measures the feedwater ETA and confirms the diagnosis.

The root cause of the over feed was determined to be inadequate dilution of the ETA feed tank. In this case, the operator only had to make one additional plant measurement to completely diagnose the problem.

EXAMPLE 3: DIAGNOSIS OF A CONDENSER LEAK

A condenser leak will lead to increased impurity concentrations in the boiler water and corrosion of the steam generator and other components within the plant.

In this example, the SDF processor 38 verifies the sodium and chloride concentrations in the steam generator blowdown and that there is an increase in the measured cation conductivity throughout the system. The expert system 50 uses the same logic and rule base 52 as previously described to validate the measurements and compares the validated data to the baseline chemistry of FIGS. 5–8.

Figure 13:
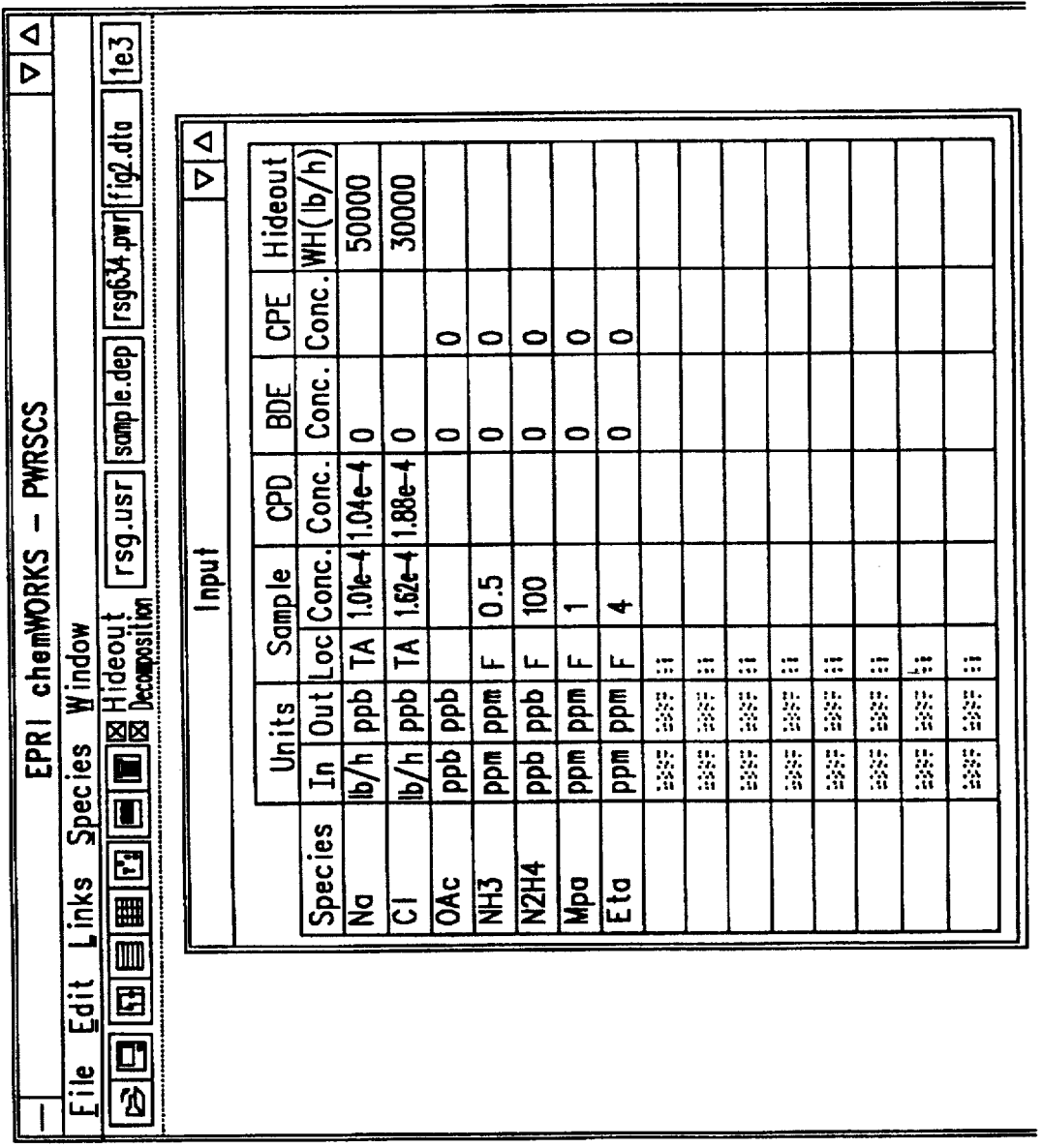
FIG. 13 illustrates a graphical user interface displaying condenser leak input information in accordance with Example 3 discussed below.

The expert system 50 recognizes that the feedwater chemistry has changed so that the source of increase is likely due to ingress into the system and not a change in steam generator behavior as diagnosed in Example 1. Since the condensate and condensate polisher effluent cation conductivity have both increased, it is likely that the source of ingress is upstream of the condensate polishers. However, the expert system 50 checks this hypothesis by running the simulator 54 with a varied ingress source term downstream of the polishers. This is done to determine if the measured or observed chemistry can be established by a source downstream of the polishers. A low probability is assigned to the rule defined for this as a cause of the increase. The expert system 50 then verifies that the measured chemistry can be obtained by condenser in leakage with a known composition of cooling water if the condensate polishers have been exhausted by the in leakage. FIGS. 13 and 14 show the input and output corresponding to firing a rule which would establish that the condenser leakage is likely the problem.

The expert system 50 verifies that the inlet and outlet cation conductivities to the condensate polishers are nominally equal and fires a rule excepting a condenser leak as the most probably source for the measured increase in the system. Thus, the expert system 50 searches for a condenser leak.

In this case, the operator does not have to wait for a detailed analysis of the composition of the water in the condensate and feedwater to determine that the source of ingress was a condenser leak.

EXAMPLE 4: DIAGNOSIS OF INGRESS OF ORGANIC CONTAMINATION IN THE SECONDARY SYSTEM OF A PWR

There are several potential sources of ingress of organic contaminants into the secondary system of a pressurized water reactor. One source is leakage of the polystyrene resin beads cross linked with divinyl benzene and used for condensate polishing and blowdown demineralization. The second source of organics is from the decomposition of organic amines used for pH control, such as morpholine or ETA. In addition to these two sources, organics can enter via makeup water, as an impurity in additives to the system or as greases and oils. Organics can cause accelerated corrosion of plant components and complicate analytical measurements of other species.

In any event, organic chemicals normally decompose at the operating temperatures and pressures of a pressurized water reactor. The decomposition products are generally short chain carboxylic acids such as: acetic, formic and glycolic acid. Other low molecular weight compounds may be byproducts of organic decomposition reactions, such as carbon dioxide. The ingress normally produces some acetate in the system and therefore the measured acetate concentration in the system can be used to track the source of the parent organic compound.

A baseline of organics will normally exist in the secondary system from amines added for pH control. The simulator 54 allows for the formation of organics such as acetate from the decomposition of amines. Due to the difficulty in predicting these decomposition reactions a priori, the simulator 54 is fit to the plant baseline chemistry data by adjustable decomposition rate constants. The concentrations of acetate generated in the system from the baseline chemistry was shown in FIGS. 6 and 7. The rate constants used were fitted to plant data for three locations in the steam cycle. By this technique, the simulator 54 is able to predict the change in organic levels associated with a change in amine feedrate. The expert system 50 can compare these changes to those predicted from ingress from another source. If, for example, the acetate concentration in the system increased from the baseline, the source would be diagnosed by the expert system 50 as follows.

After verification of the acetate concentration using the methodology previously described, the expert system 50 determines how much the amine concentration must change to produce the new level of acetates. In this example, we will assume that the acetate level in the steam generator increased from its baseline value of 150 ppb to 595 ppb. An ETA level of nominally 6.14 ppm in the feedwater is required to match the new acetate level as shown in FIG. 15. The expert system 50 then checks to see if the measured pH and specific conductivity have also changed in accordance with the predicted values shown in FIG. 15. In this case, the pH did not change as much as required so that the expert system 50 concludes that it is likely that either the decomposition rate of the amine has changed or there is a new source of organics in the system.

The decomposition rate can be changed to match the observed acetate in the system. The results of adjusting the decomposition rate constants to match the new acetate concentration is shown in FIG. 16. As shown in FIG. 16, the predicted change in amine concentration, pH and specific conductivity are small. However, the amount the decomposition rate constants would have to change is excessive, and therefore the expert system 50 considers it more probable that a new source of organics exists in the system. Three other sources must be tested. The first source, chemical in leakage, is evaluated by increasing the acetate level in the in leakage stream from the baseline of zero. The second source tested is acetate in the makeup water. This is evaluated by inputting acetate as condenser in leakage. The third source is modeled by increasing the condensate concentration from its baseline value. In this case, the acetate levels can be matched by either chemical in leakage (treatment additive), or by increasing condensate polisher leakage. The latter case, however, also would increase the condensate polisher effluent specific conductivity and cation conductivity, whereas increasing the chemical in leakage produces the same base line condensate polisher effluent values. In this example, it is assumed that the measured polisher effluent conductivity also increases, which makes it likely that the source of acetate increase was due to saturation of the condensate polishers. Consequently, the plant operator is advised to regenerate the condensate demineralizers.

EXAMPLE 5: DATA COLLECTION OPTIMIZATION

The artificial intelligence processor 40 can be used to optimize the number of measurements which must be made to describe the chemistry throughout the system. As previously described, the analytical models used in the expert system 50 are over specified by the number of measurements made in the system. The SDF processor 38 is used to determine the best estimate of each measurement in the plant and the accuracy of the estimate. By allowing the user of the expert system 50 to specify the required accuracy of the model predictions, the user can evaluate what the impact of reducing the number or frequency of measurements is on the overall accuracy of the system predictions. The user can then eliminate measurements which do not significantly improve the overall accuracy of the model predictions. Likewise, the user can fine tune the model predictions by making supplemental measurements of plant chemistry parameters. In this way, the user can improve the conclusions of the expert system 50 by making more accurate measurements at an increased frequency.

In all of the examples discussed above, the analysis or diagnosis of the off-normal chemistry was simplified for clarity of illustration. In actual use, the plant water chemistry data 34 will not exactly agree with the model predictions as was shown in these examples. In these examples, single model inputs were adjusted to match an individual plant measurement. In practice, the expert system 50 uses routines which minimize the differences or errors between a number of measured parameters and the model inputs. This technique, in conjunction with fuzzy rule sets, will establish the best diagnosis of the chemistry.

The foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

We claim:

1. A power plant water chemistry analysis apparatus, comprising:

water chemistry sensors to obtain power plant water chemistry data characterizing the chemical activity of a power plant water system;

an analytical model processor to generate model predictions for said power plant water system; and an artificial intelligence processor to process said power plant water chemistry data and said model predictions, which in combination constitute over specified system data with more known power plant water chemistry data than unknown model predictions, said artificial intelligence processor generating power plant water chemistry diagnostic information from said over specified system data.

2. The apparatus of claim 1 wherein said artificial intelligence processor includes a power plant water chemistry system simulator to process said over specified system data.

3. The apparatus of claim 1 further comprising:

a statistical data fitting processor to select screened data from said over specified system data.

4. The apparatus of claim 3 wherein said statistical data fitting processor determines the statistical best fit of said power plant water chemistry data that satisfy the constraints given by said model predictions.

5. The apparatus of claim 1 wherein said artificial intelligence processor includes a rule base to process said over specified system data.

6. The apparatus of claim 1 wherein said artificial intelligence processor further includes a pattern recognition module to process said over specified system data.

7. A computer readable memory to direct a computer to function in a specified manner, comprising:

power plant water chemistry data characterizing the chemical activity of a power plant water system;

model predictions for said power plant water system; and executable instructions stored in said memory, said executable instructions including instructions to process said power plant water chemistry data and said model predictions, which in combination constitute over specified system data with more known power plant water chemistry data than unknown model predictions, to generate power plant water chemistry diagnostic information from said over specified system data.

8. The apparatus of claim 7 wherein said executable instructions include instructions defining a power plant water chemistry system simulator to process said over specified system data.

9. The apparatus of claim 7 wherein said executable instructions include instructions defining a statistical data fitting processor to select screened data from said over specified system data.

10. The apparatus of claim 7 wherein said executable instructions include instructions defining a rule base to process said over specified system data.

11. The apparatus of claim 7 wherein said executable instructions include instructions defining a pattern recognition module to process said over specified system data.

12. A method of analyzing power plant water chemistry, said method comprising the steps of:

accumulating power plant water chemistry data characterizing the chemical activity of a power plant water system;

generating model predictions for said power plant water system; and deriving power plant water chemistry diagnostic information from said power plant water chemistry data and said model predictions, which in combination constitute over specified system data with more known power plant water chemistry data than unknown model predictions.

13. The method of claim 12 further comprising the step of selecting screened data from said over specified system data.

14. The method of claim 12 wherein said deriving step includes the step of processing said over specified system data with a rule base.

15. The method of claim 12 wherein said deriving step includes the step of processing said over specified system data with a power plant water chemistry system simulator.

16. The method of claim 12 wherein said deriving step includes the step of processing said over specified system data with a pattern recognition module.

\* \* \* \* \*